US012551662B2

(12) United States Patent
Huang

(10) Patent No.: US 12,551,662 B2
(45) Date of Patent: Feb. 17, 2026

(54) MEDICAL INSERTION MECHANISM AND MEDICAL DEVICE THEREWITH

(71) Applicant: ALTEK BIOTECHNOLOGY CORPORATION, Hsinchu (TW)

(72) Inventor: Yu-Cheng Huang, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 683 days.

(21) Appl. No.: 17/992,954

(22) Filed: Nov. 23, 2022

(65) Prior Publication Data

US 2024/0165376 A1 May 23, 2024

(51) Int. Cl.
*A61M 25/06* (2006.01)
*A61M 5/158* (2006.01)

(52) U.S. Cl.
CPC ............ *A61M 25/06* (2013.01); *A61M 5/158* (2013.01); *A61M 2005/1585* (2013.01)

(58) Field of Classification Search
CPC .................. A61M 25/06; A61M 5/158; A61M 2005/1585; A61M 5/2033; A61M 5/3287; A61M 2005/14252; A61M 2005/1583; A61M 2005/2006; A61M 2005/2026; A61M 5/14248
See application file for complete search history.

(56) References Cited

U.S. PATENT DOCUMENTS

| | | | |
|---|---|---|---|
| 6,179,569 | B1 | 1/2001 | Kojima |
| 10,569,011 | B2 | 2/2020 | Dilanni |
| 11,083,840 | B2 | 8/2021 | Gibson |
| 2005/0245956 | A1 | 11/2005 | Steinemann |
| 2015/0196719 | A1 | 7/2015 | Uchiyama |
| 2021/0220555 | A1 | 7/2021 | Stefanov |
| 2021/0379282 | A1 | 12/2021 | O'Connor |

FOREIGN PATENT DOCUMENTS

| | | | |
|---|---|---|---|
| CN | 102378638 | A | 3/2012 |
| CN | 112292166 | | 1/2021 |
| CN | 112869909 | A | 6/2021 |
| CN | 113209420 | A | 8/2021 |
| CN | 115025316 | A | 9/2022 |
| EP | 3616737 | A2 | 3/2020 |

*Primary Examiner* — Cris L. Rodriguez
(74) *Attorney, Agent, or Firm* — Winston Hsu

(57) ABSTRACT

A medical insertion mechanism is provided and includes a base, a needle holder slidably disposed on the base, a needle disposed on the needle holder, a cannula holder arranged at a position corresponding to the needle holder, a cannula disposed on the cannula holder, a pivoting assembly pivotally disposed on the base, a lever movably disposed on the base and movably engaged with the pivoting assembly, an actuator disposed on the base, and a driving component for driving the pivoting assembly to pivot when the actuator slides to disengage from the pivoting assembly. When the pivoting assembly pivots, the lever drives the needle holder to slide along an insertion direction and then along a retraction direction, so as to insert the cannula into the patient's body. Besides, a medical device having the aforementioned medical insertion mechanism is also provided.

20 Claims, 14 Drawing Sheets

MEDICAL INSERTION MECHANISM AND MEDICAL DEVICE THEREWITH

BACKGROUND OF THE INVENTION

1. Field of the Invention

The present invention relates to a medical insertion mechanism and a medical device therewith, and more specifically, to a medical insertion mechanism with simple structure, compact size, easy operation and precise insertion and retraction function, and a medical device therewith.

2. Description of the Prior Art

A medical device, e.g., an on-body injector, is designed to deliver a dose of a drug. However, the conventional on-body injectors available in the markets fail to meet requirements of simple structure, compact size, easy operation and precise insertion and retraction function. Therefore, an improvement of the medical device is urgently needed.

SUMMARY OF THE INVENTION

It is an objective of the present invention to provide a medical insertion mechanism with simple structure, compact size, easy operation and precise insertion and retraction function, and a medical device therewith for solving the aforementioned problem.

In order to achieve the aforementioned objective, the present invention discloses a medical insertion mechanism. The medical insertion mechanism includes a base, a needle holder, a needle, a cannula holder, a cannula, a pivoting assembly, a lever, an actuator and a driving component. The needle holder is disposed on the base and slidable relative to the base along an insertion direction or a retraction direction opposite to the insertion direction. The needle holder includes a pushing structure. The needle is disposed on the needle holder. The cannula holder is arranged at a position corresponding to the needle holder. The pushing structure is configured to abut against the cannula holder along the insertion direction. The cannula is disposed on the cannula holder. The pivoting assembly is disposed on the base and pivotable relative to the base from a first position through a second position to a third position. The lever is movably disposed on the base and movably engaged with the pivoting assembly and the needle holder. The actuator is slidably disposed on the base. The actuator includes an abutting structure configured to slidably engage with or disengage from the pivoting assembly. The driving component is configured to drive the pivoting assembly to pivot from the first position through the second position to the third position when the abutting structure slidably disengages from the pivoting assembly. When the pivoting assembly pivots from the first position to the second position, the lever drives the needle holder and the cannula holder to slide along the insertion direction, so as to drive the needle and the cannula to move along the insertion direction together. When the pivoting assembly pivots from the second position to the third position, the lever drives the needle holder to slide along the retraction direction to drive the needle to retract relative to the cannula.

In order to achieve the aforementioned objective, the present invention further discloses a medical device. The medical device includes a case and a medical insertion mechanism. The medical insertion mechanism includes a base, a needle holder, a needle, a cannula holder, a cannula, a pivoting assembly, a lever, an actuator and a driving component. The base is disposed on the case. The needle holder is disposed on the base and slidable relative to the base along an insertion direction or a retraction direction opposite to the insertion direction. The needle holder includes a pushing structure. The needle is disposed on the needle holder. The cannula holder is arranged at a position corresponding to the needle holder. The pushing structure is configured to abut against the cannula holder along the insertion direction. The cannula is disposed on the cannula holder. The pivoting assembly is disposed on the base and pivotable relative to the base from a first position through a second position to a third position. The lever is movably disposed on the base and movably engaged with the pivoting assembly and the needle holder. The actuator is slidably disposed on the base. The actuator includes an abutting structure configured to slidably engage with or disengage from the pivoting assembly. The driving component is configured to drive the pivoting assembly to pivot from the first position through the second position to the third position when the abutting structure slidably disengages from the pivoting assembly. When the pivoting assembly pivots from the first position to the second position, the lever drives the needle holder and the cannula holder to slide along the insertion direction, so as to drive the needle and the cannula to move along the insertion direction together. When the pivoting assembly pivots from the second position to the third position, the lever drives the needle holder to slide along the retraction direction to drive the needle to retract relative to the cannula.

In summary, the present invention has less parts and compact size. Besides, in the present invention, when it is desired to use the medical device for drug injection or fluid drainage, it only has to operate the operating component to drive the actuator to slide for slidably disengaging the abutting structure of the actuator from the protruding structure of the pivoting assembly, so that the cannula can be inserted into the patient's body. Therefore, the present invention has easy operation and precise insertion and retraction function.

These and other objectives of the present invention will no doubt become obvious to those of ordinary skill in the art after reading the following detailed description of the preferred embodiment that is illustrated in the various figures and drawings.

DETAILED DESCRIPTION

In the following detailed description of the preferred embodiments, reference is made to the accompanying drawings which form a part hereof, and in which is shown by way of illustration specific embodiments in which the invention may be practiced. In this regard, directional terminology, such as “top”, “bottom”, “left”, “right”, “front”, “back”, etc., is used with reference to the orientation of the Figure(s) being described. The components of the present invention can be positioned in a number of different orientations. As such, the directional terminology is used for purposes of illustration and is in no way limiting. Accordingly, the drawings and descriptions will be regarded as illustrative in nature and not as restrictive. Also, if not specified, the term “connect” or “couple” is intended to mean either an indirect or direct electrical/mechanical connection. Thus, if a first device is connected or coupled to a second device, that connection may be through a direct electrical/mechanical connection, or through an indirect electrical/mechanical connection via other devices and connections.

Figure 1:
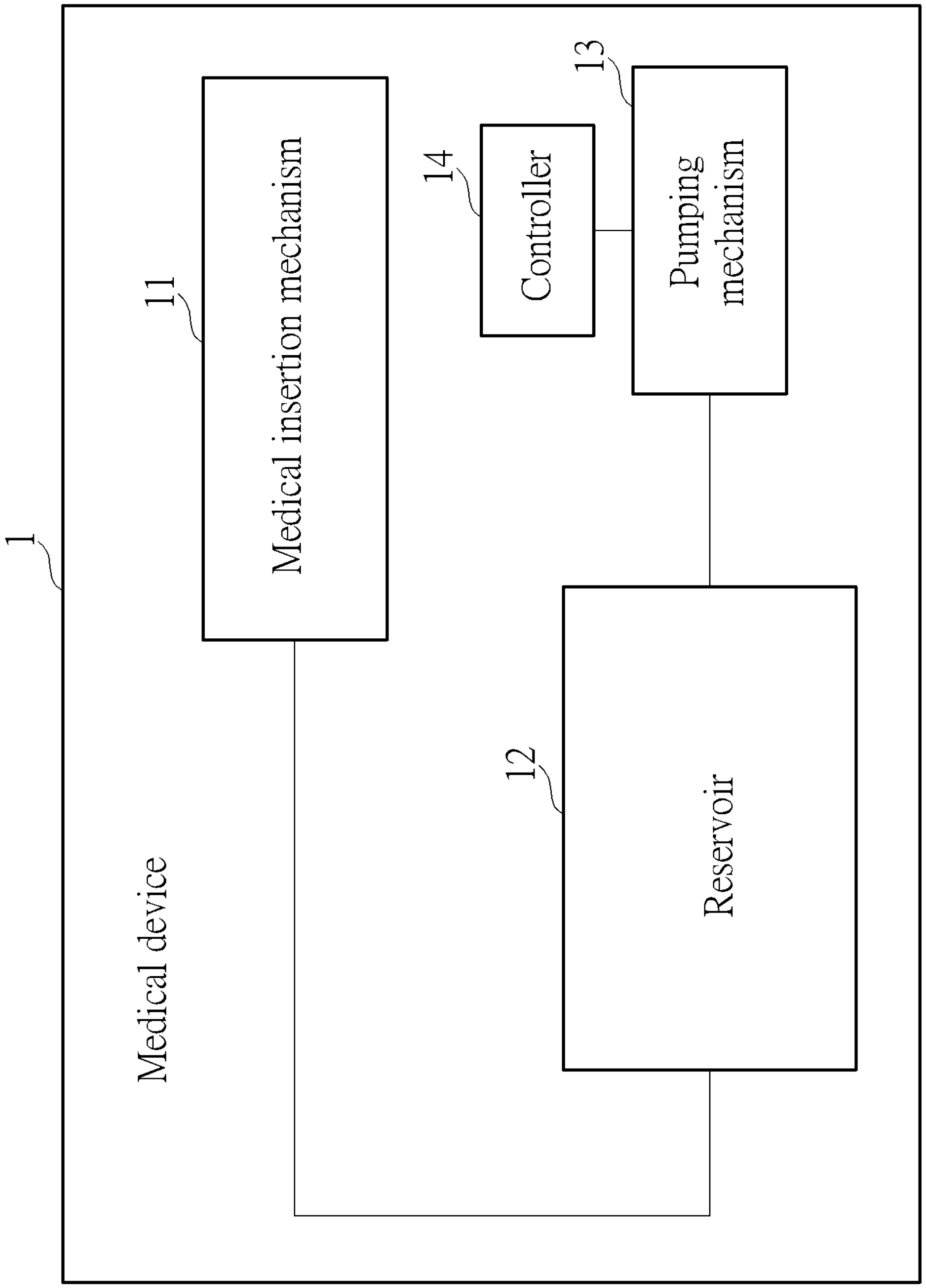
FIG. 1 is a block diagram of a medical device according to an embodiment of the present invention.
Figure 2:
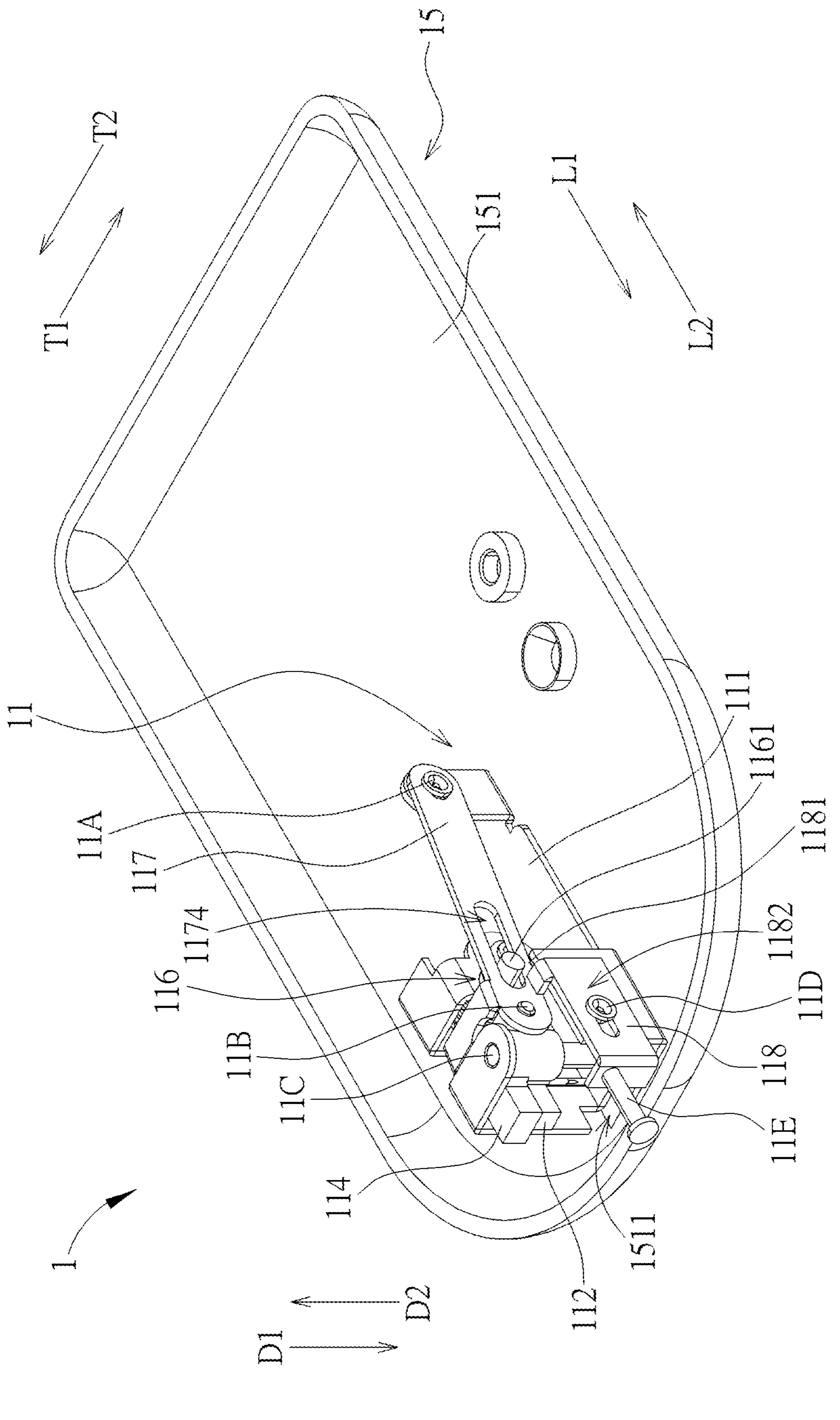
FIG. 2 and FIG. 3 are partial diagrams of the medical device at different views according to the embodiment of the present invention.
Figure 3:
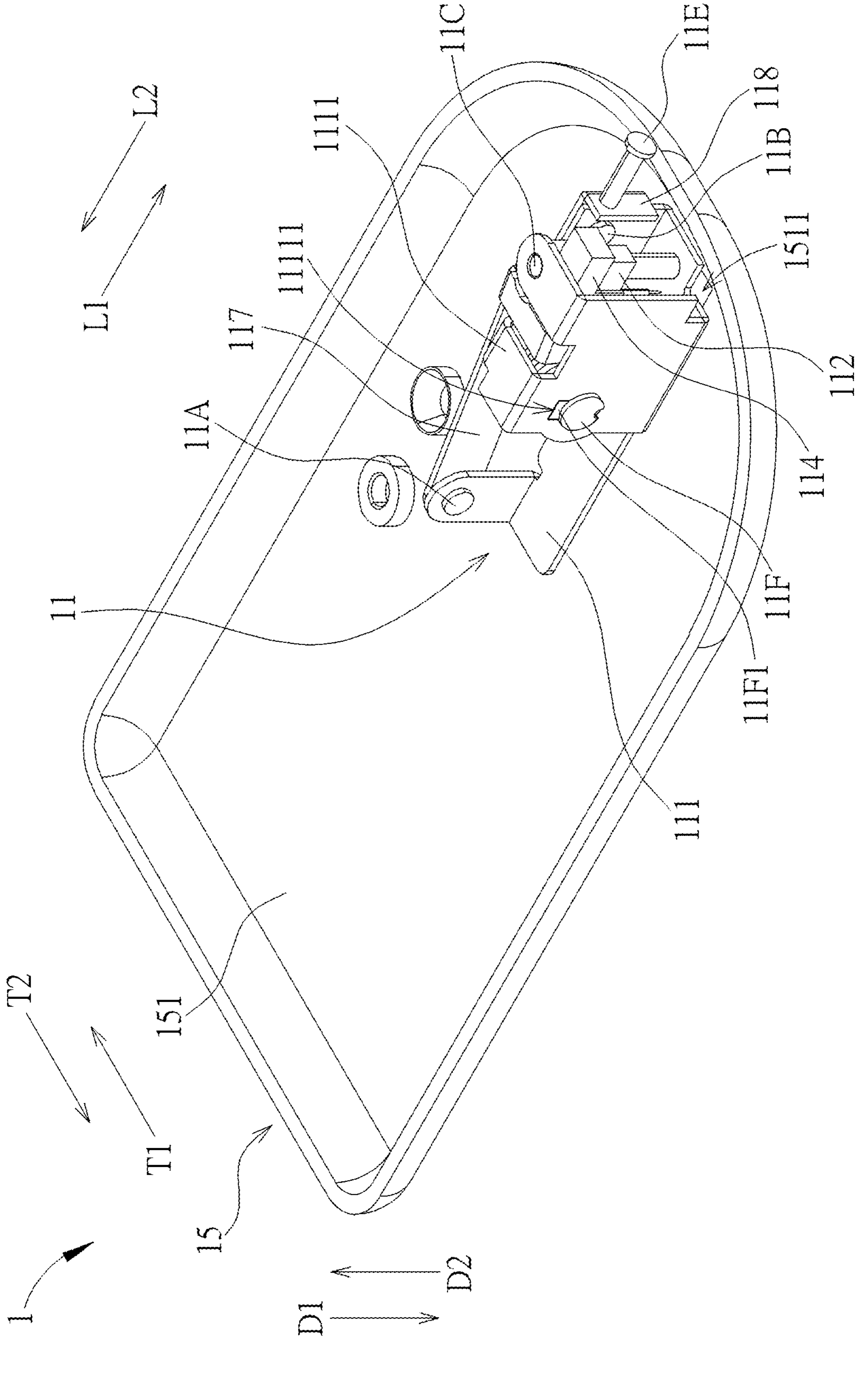
Figure 4:
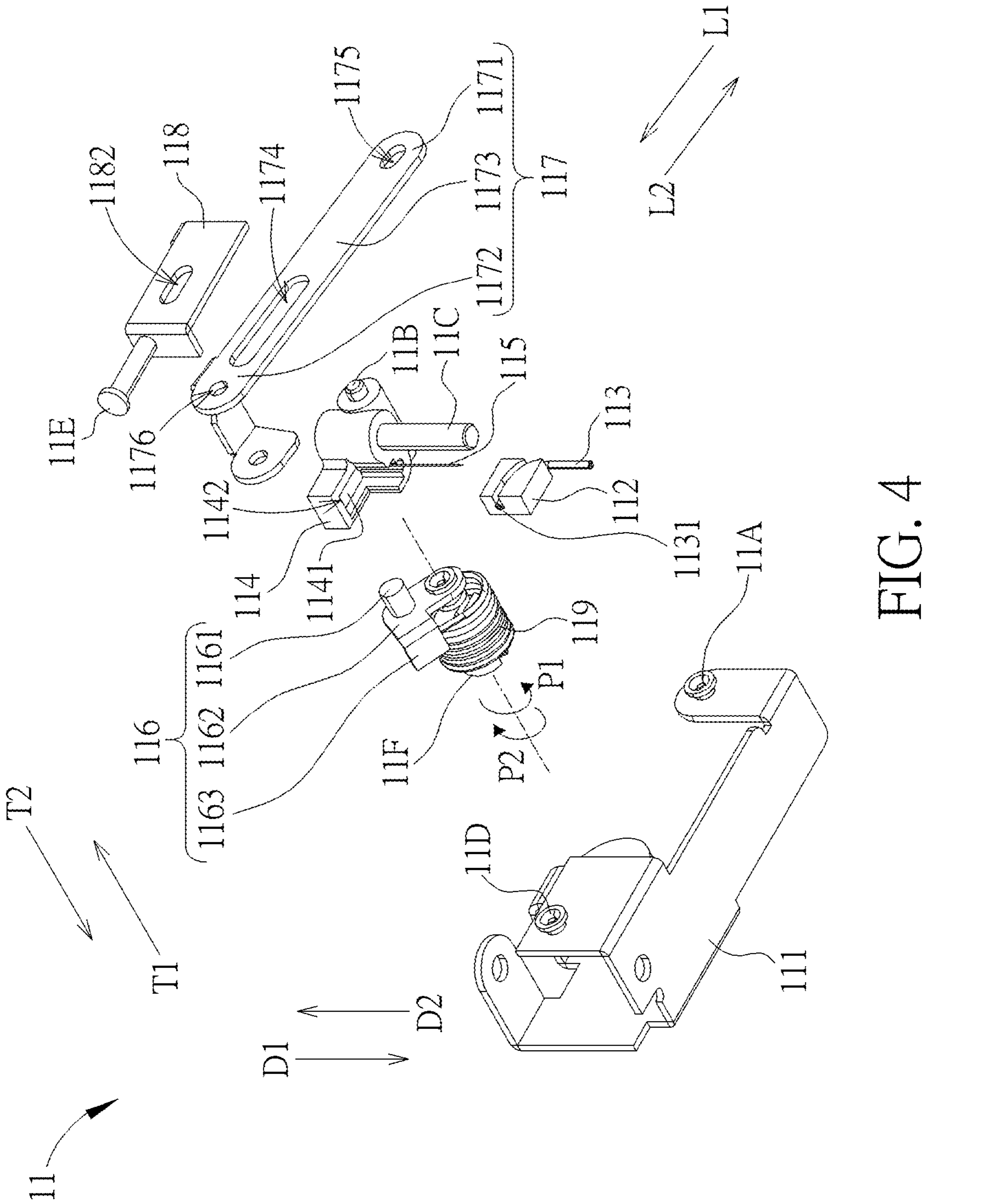
FIG. 4 and FIG. 5 are partial exploded diagrams of a medical insertion mechanism of the medical device at different views according to the embodiment of the present invention.
Figure 5:
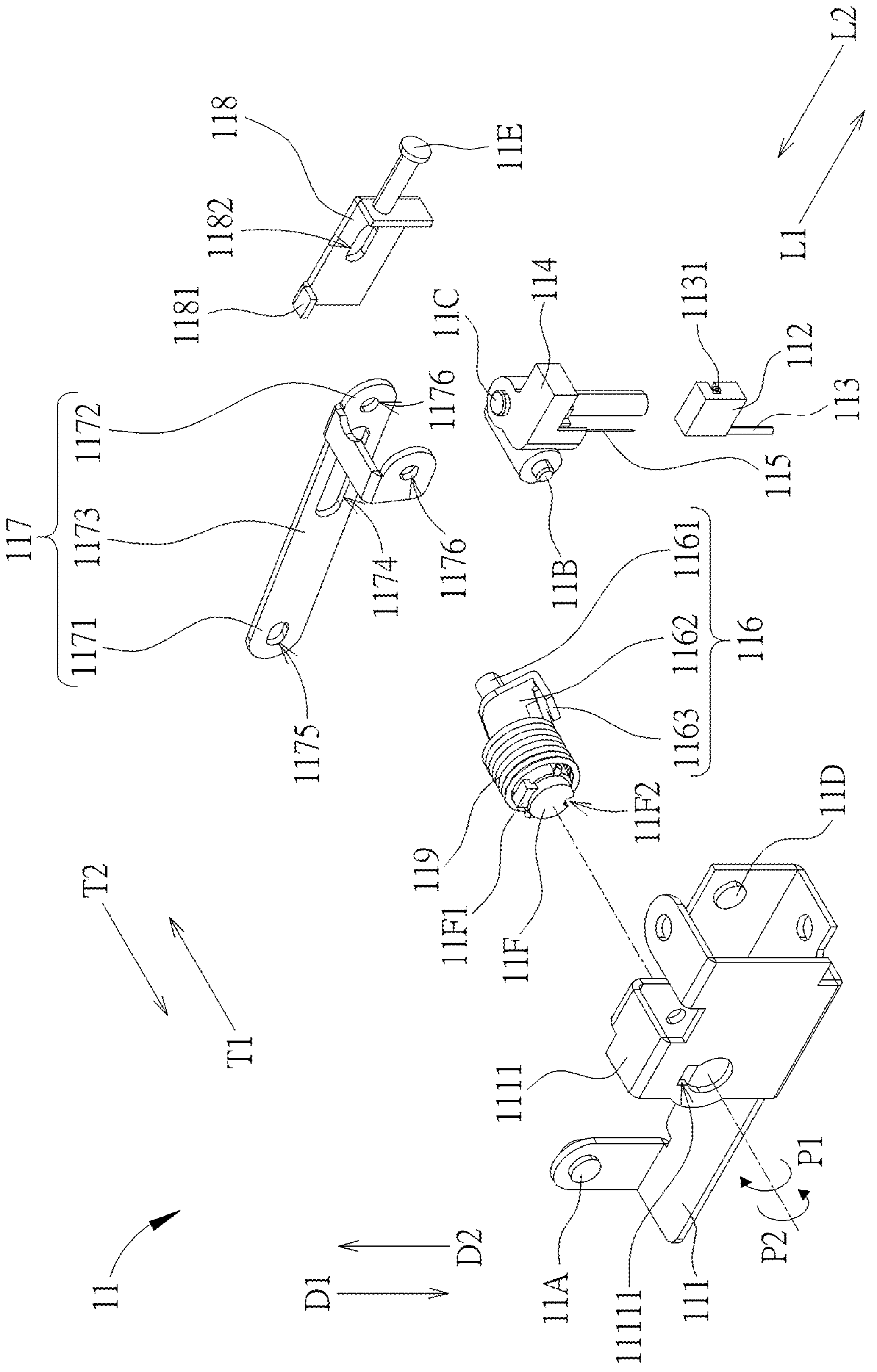
Figure 6:
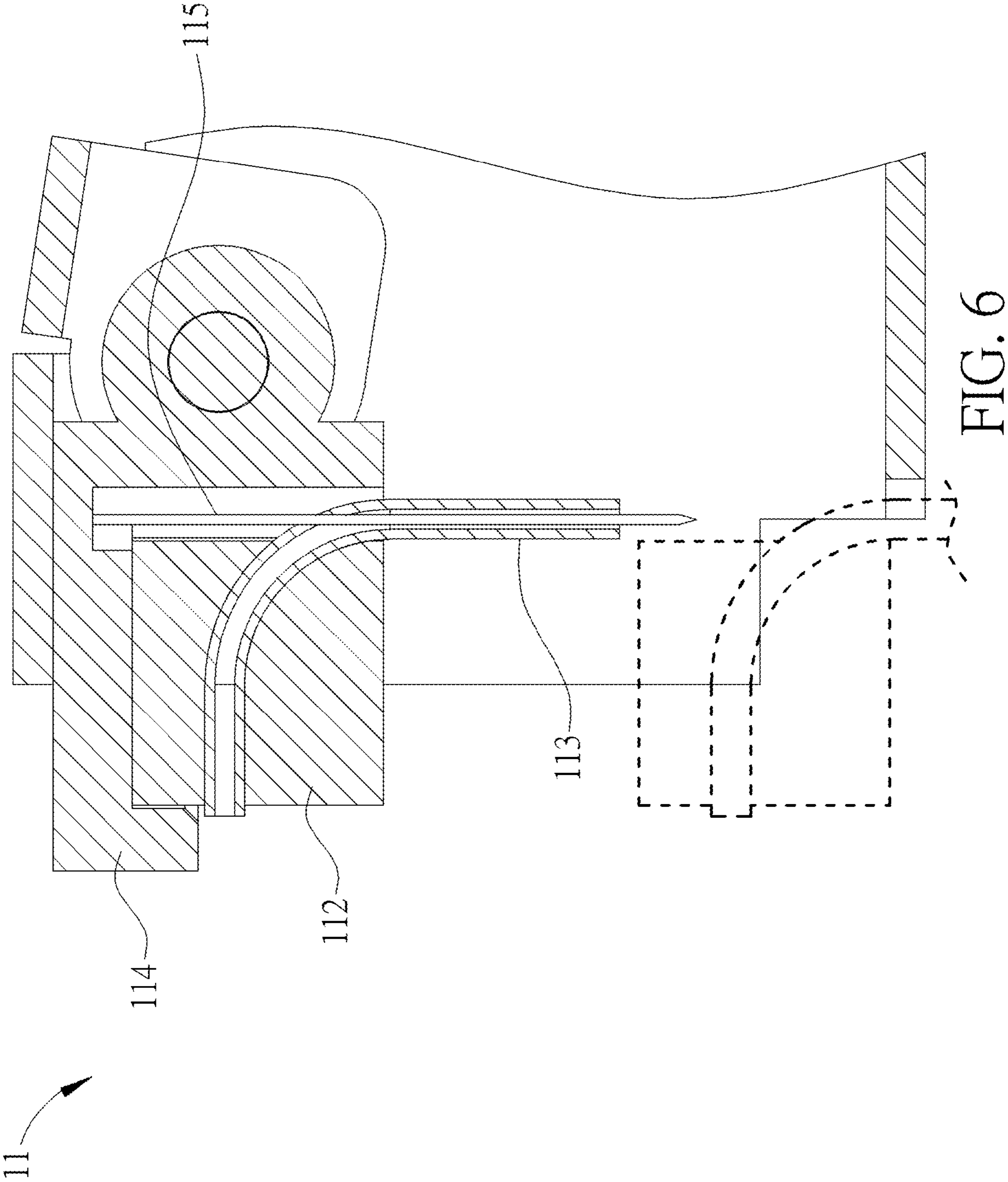
FIG. 6 is a partial sectional diagram of the medical insertion mechanism according to the embodiment of the present invention.

Please refer to FIG. 1 to FIG. 6. FIG. 1 is a block diagram of a medical device 1 according to an embodiment of the present invention. FIG. 2 and FIG. 3 are partial diagrams of the medical device 1 at different views according to the embodiment of the present invention. FIG. 4 and FIG. 5 are partial exploded diagrams of a medical insertion mechanism 11 of the medical device 1 at different views according to the embodiment of the present invention. FIG. 6 is a partial sectional diagram of the medical insertion mechanism 11 according to the embodiment of the present invention. As shown in FIG. 1 to FIG. 6, in this embodiment, the medical device 1 can be an on-body injector for drug injection. However, the present invention is not limited to this embodiment. For example, in another embodiment, the medical device can be a trocar for fluid drainage. The medical device 1 includes the medical insertion mechanism 11. The medical insertion mechanism 11 includes a base 111, a cannula holder 112, a cannula 113, a needle holder 114, a needle 115, a pivoting assembly 116, a lever 117, an actuator 118 and a driving component 119. The needle holder 114 is disposed on the base 111 and slidable relative to the base 111 along an insertion direction D1 or a retraction direction D2 opposite to the insertion direction D1. The needle holder 114 includes a pushing structure 1141. The needle 115 is disposed on the needle holder 114. The cannula holder 112 is arranged at a position corresponding to the needle holder 114. The pushing structure 1141 is configured to abut against the cannula holder 112 along the insertion direction D1. The cannula 113 is disposed on the cannula holder 112. The cannula 113 is configured to provide a drug passage or a fluid passage. In this embodiment, as shown in FIG. 4, a positioning recess 1142 can be formed on the needle holder 114 for at least partially receiving the cannula holder 112, and the pushing structure 1141 can be a wall of the positioning recess 1142. Besides, as shown in FIG. 6, in this embodiment, the needle 115 can be a hollow structure or a solid structure at least partially disposed inside the cannula 113 in a removable penetrating manner, and the cannula 113 can be made of a resealable material for preventing leakage. However, the present invention is not limited to this embodiment.

In this embodiment, in order for drug injection, as shown in FIG. 1, the medical device 1 further includes a reservoir 12, a pumping mechanism 13 and a controller 14. The reservoir 12 is for drug storage and is communicated with the cannula 113 via a flexible tube connected between a port 1131 of the cannula 113 and a port of the reservoir 12. The controller 12 is configured to control the pumping mechanism 13 to pump a drug to flow from the reservoir 12 to the cannula 113 through the flexible tube. The pumping mechanism 13 can but not limited to include an electric motor, a plunger slidably disposed in the reservoir 12 and a reducer connected between the electric motor and the plunger. The controller 14 can be a micro processing unit (MCU), a processor, or an application specific integrated circuit (ASIC) for controlling the motor to drive the plunger to slide to pump the drug out of the reservoir 12. However, the structures of the pumping mechanism and the medical device are not limited to this embodiment. It depends on practical demands.

Besides, as shown in FIG. 2 to FIG. 5, the pivoting assembly 116 is disposed on the base 111 and pivotable relative to the base 111. The lever 117 is movably disposed on the base 111 and movably engaged with the pivoting assembly 116 and the needle holder 114. The actuator 118 is disposed on the base 111 and slidable relative to the base 111 along an unlocking direction L1 perpendicular to the insertion direction D1, or along a locking direction L2 opposite to the unlocking direction L1. The actuator 118 includes an abutting structure 1181 configured to slidably engage with the pivoting assembly 116 along the locking direction L2 or disengage from the pivoting assembly 116 along the unlocking direction L1. The driving component 119 is configured to drive the pivoting assembly 116 to pivot along a first pivoting direction P1 around a pivoting axis perpendicular to the unlocking direction L1 and the insertion direction D1 when the abutting structure 1181 slidably disengages from the pivoting assembly 116. When the pivoting assembly 116 pivots along the first pivoting direction P1, the lever 117 drives the needle holder 114 to slide along the insertion direction D1 and then to slide along the retraction direction D2. When the lever 117 drives the needle holder 114 to slide along the insertion direction D1, the needle holder 114 pushes the cannula holder 112 to slide together with the needle holder 114 by the pushing structure 1141, so as to drive the needle 115 and the cannula 113 to move along the insertion direction D1 together for insertion of the needle 115 and the cannula 113 into a patient's body along the insertion direction D1. When the lever 117 drives the needle holder 114 to slide along the retraction direction D2, the lever 117 drives the needle holder 114 to slide along the retraction direction D2 to drive the needle 115 to retract relative to the cannula 113 along the retraction direction D2 for withdrawing the needle 115 from the patient's body along the retraction direction D2 and leaving the cannula 113 inserted in the patient's body.

In order to improve convenience of use, the cannula 113 can be made of flexible material. The needle 115 can be made of rigid material, and a length of the cannula 113 along a direction parallel to the insertion direction D1 and the retraction direction D2 can be less than a length of the needle 115 along the direction parallel to the insertion direction D1 and the retraction direction D2.

Figure 10:
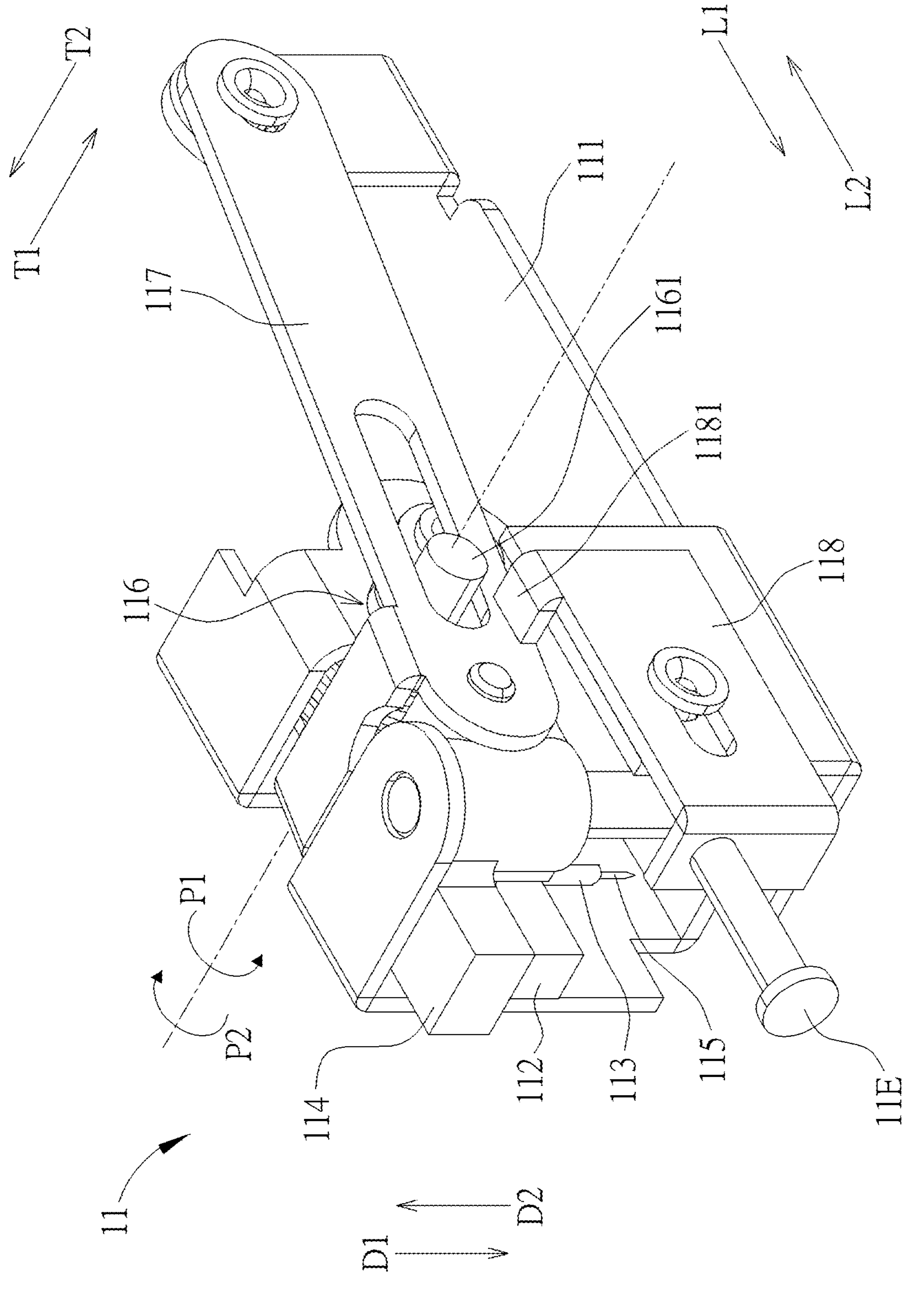
FIG. 10 is a partial diagram of the medical insertion mechanism in a second state according to the embodiment of the present invention.
Figure 12:
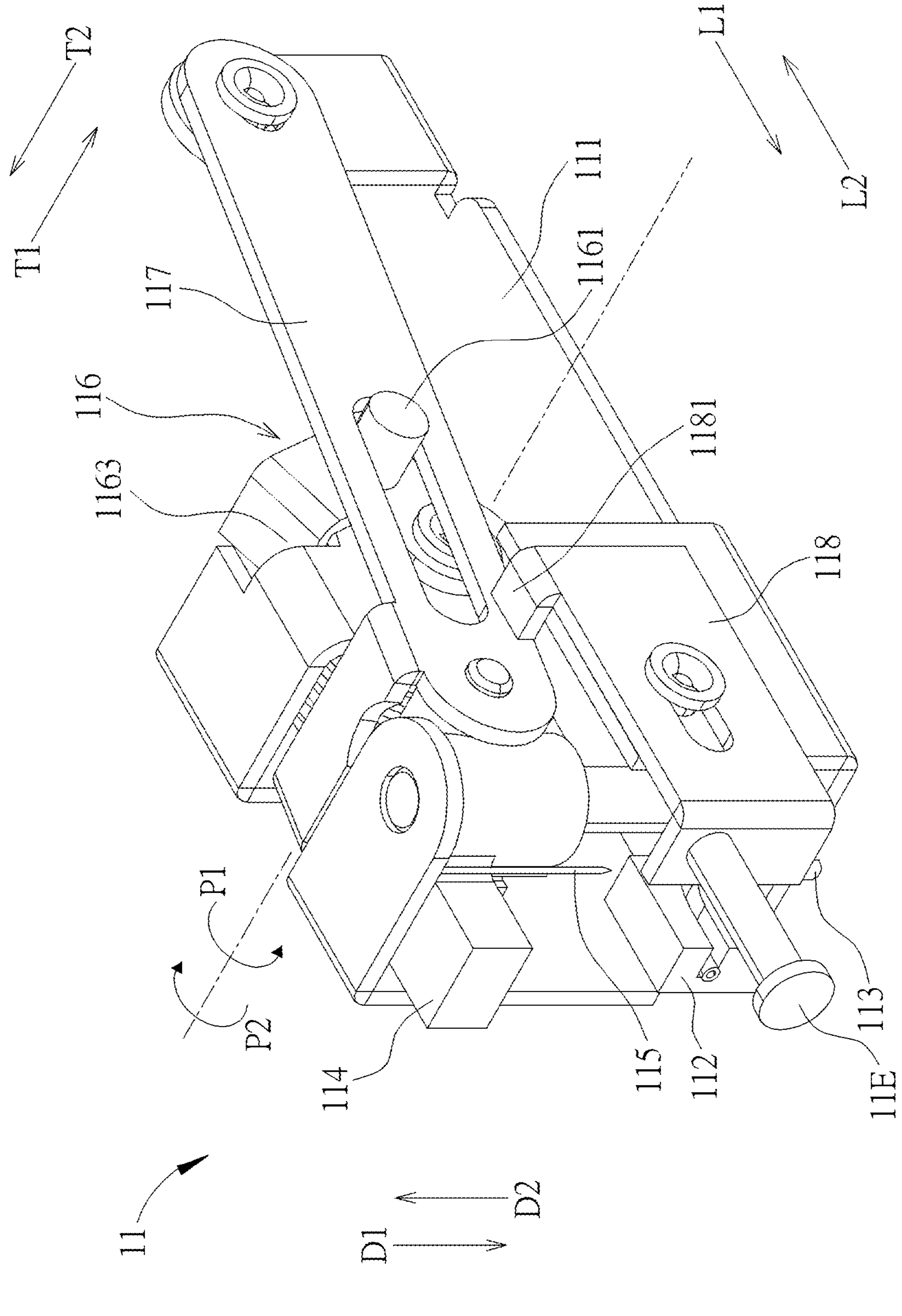
FIG. 12 is a partial diagram of the medical insertion mechanism in a fourth state according to the embodiment of the present invention.

Furthermore, in this embodiment, the lever 117 can be driven by the pivoting assembly 116 to drive the needle holder 114 to slide from an original position (as shown in FIG. 10) along the insertion direction D1 and then back to the original position (as shown in FIG. 12) along the retraction direction D2 when the pivoting assembly 116 pivots along the first pivoting direction P1. However, the present invention is not limited to this embodiment. For example, in another embodiment, the lever can be configured to drive the needle holder to slide from the original position and then back to a non-original position which may be higher or lower than the original position when the pivoting assembly pivots along the first pivoting direction.

As shown in FIG. 2 and FIG. 3, the medical device 1 further includes a case 15 for preventing damage of the medical insertion mechanism 11. The case 15 includes a first mounting part 151 and a second mounting part, which is not shown in the figures, detachable installed on the first mounting part 151. The first mounting part 151 has an aperture 1511, so that the needle 115 and the cannula 113 can pass through the aperture 1511 to be inserted into the patient's body. The base 111 is mounted on the first mounting part 151. However, the present invention is not limited to this embodiment.

As shown in FIG. 2 to FIG. 5, the lever 117 is located between the pivoting assembly 116 and the actuator 118 and includes a first end 1171, a second end 1172 and a middle portion 1173 between the first end 1171 and the second end 1172. The pivoting assembly 116 is engaged with a longitudinal slot 1174 formed on the middle portion 1173 of the lever 117 between a first end 1171 and a second end 1172 of the lever 117. The base 111 is movably connected to the first end 1171 of the lever 117. The needle holder 114 is movably connected to the second end 1172 of the lever 117.

Specifically, the longitudinal slot 1174 is adjacent to the second end 1172 of the lever 117 and away from the first end 1171 of the lever 117. The lever 117 has a first side and a second side opposite to the first side. The cannula holder 112 and the needle holder 114 are located at the first side of the lever 117. The pivoting assembly 116 includes a protruding structure 1161 passing through the longitudinal slot 1174 and movable relative to the longitudinal slot 1174, and the pivoting assembly 116 further includes a pivoting body 1162 located at the first side of the lever 117. The protruding structure 1161 protrudes from the pivoting body 1162. The abutting structure 1181 is located at the second side of the lever 117 and configured to abut against the protruding structure 1161. The aforementioned configuration can achieve compact size and labor saving. However, the present invention is not limited to this embodiment. For example, the longitudinal slot can be adjacent to the first end of the lever and away from the second end of the lever, and the needle holder and the cannula holder can be located at the second side of the lever.

Besides, an elongated hole 1175 is formed on the first end 1171 of the lever 117. Two circular holes 1176 are formed on the second end 1172 of the lever 117. The medical insertion mechanism 11 further includes a connecting pin 11A disposed on the base 111 and a driving pin 11B disposed on the needle holder 114. The connecting pin 11A passes through the elongated hole 1175 and is movable relative to the elongated hole 1175. Two ends of the driving pins 11B respectively pass through the circular holes 1176 and are movable relative to the circular holes 1176. By a cooperation of the connecting pin 11A and the elongated hole 1175, a cooperation of the driving pin 11B and the circular holes 1176, and a cooperation of the protruding structure 1161 and the longitudinal slot 1174, a pivoting movement of the pivoting assembly 116 relative to the base 111 can drive the lever 117 to pivot relative to the base 111 to drive the needle holder 114 to slide along the insertion direction D1 and/or the retraction direction D2. However, the present invention is not limited to this embodiment. For example, in another embodiment, there can be only one circular hole formed on the second end of the lever and one driving pin disposed on the needle holder. Alternatively, in another embodiment, the circular hole and the elongated hole can be respectively formed on the first end and the second end of the lever, and the connecting pin and the driving pin can respectively pass through the circular hole and the elongated hole and respectively be movable relative to the circular hole and the elongated hole. Alternatively, in another embodiment, the circular hole and the elongated hole can be respectively formed on the needle holder and the base, and the driving pin and the connecting pin can be respectively disposed on the second end of the lever and the first end of the lever.

As shown in FIG. 2 to FIG. 5, in other to ensure the needle 115 and the cannula 113 to be driven to move along the insertion direction D1 when the pivoting assembly 116 pivots along the first pivoting direction P1, the medical insertion mechanism 11 further includes a guiding component 11C disposed on the base 111 and configured to guide the needle holder 114 and the cannula holder 112 to slide along the insertion direction D1. In this embodiment, the guiding component 11C can be a guiding column passing through the needle holder 114. However, the present invention is not limited to this embodiment. For example, in another embodiment, the guiding component can be a guiding column passing through the needle holder and the cannula holder or passing through the cannula holder only, or the guiding component can be a guiding track configured to cooperate with at least one of the needle holder and the cannula holder.

Furthermore, in order to achieve compact size, in this embodiment, the lever 117 can be engaged with a portion of the needle holder 114 located between the pivoting assembly 116 and the guiding component 11C by the driving pin 11B. However, the present invention is not limited to this embodiment. For example, in another embodiment, the lever can be engaged with a portion of the needle holder located at a side of the guiding component away from the pivoting assembly.

As shown in FIG. 4 and FIG. 5, the pivoting assembly 116 further includes a stopping structure 1163 extending from the pivoting body 1162 and configured to contact with the base 111 for stopping the pivoting assembly 116 to prevent an excessive pivoting movement of the pivoting assembly 116, when the pivoting assembly 116 pivots along the first pivoting direction P1.

In addition, as shown in FIG. 2 to FIG. 5, in order to achieve a sliding configuration of the actuator 118 relative to the base 111, a sliding slot 1182 is formed on the actuator 118, the medical insertion mechanism 11 further includes a sliding pin 11D disposed on the base 111, and the sliding pin 11D passes through the sliding slot 1182, such that the actuator 118 is movable relative to the sliding pin 11D via the sliding slot 1182.

In this embodiment, the medical insertion mechanism 11 can further include an operating component 11E connected to the actuator 118 and exposed out of the base 111 and/or the case 15 for easy manual operation. However, the present invention is not limited to this embodiment. For example, the actuator can be driven to slide by a linking mechanism actuated by an electric motor or a pneumatic motor.

Figure 7:
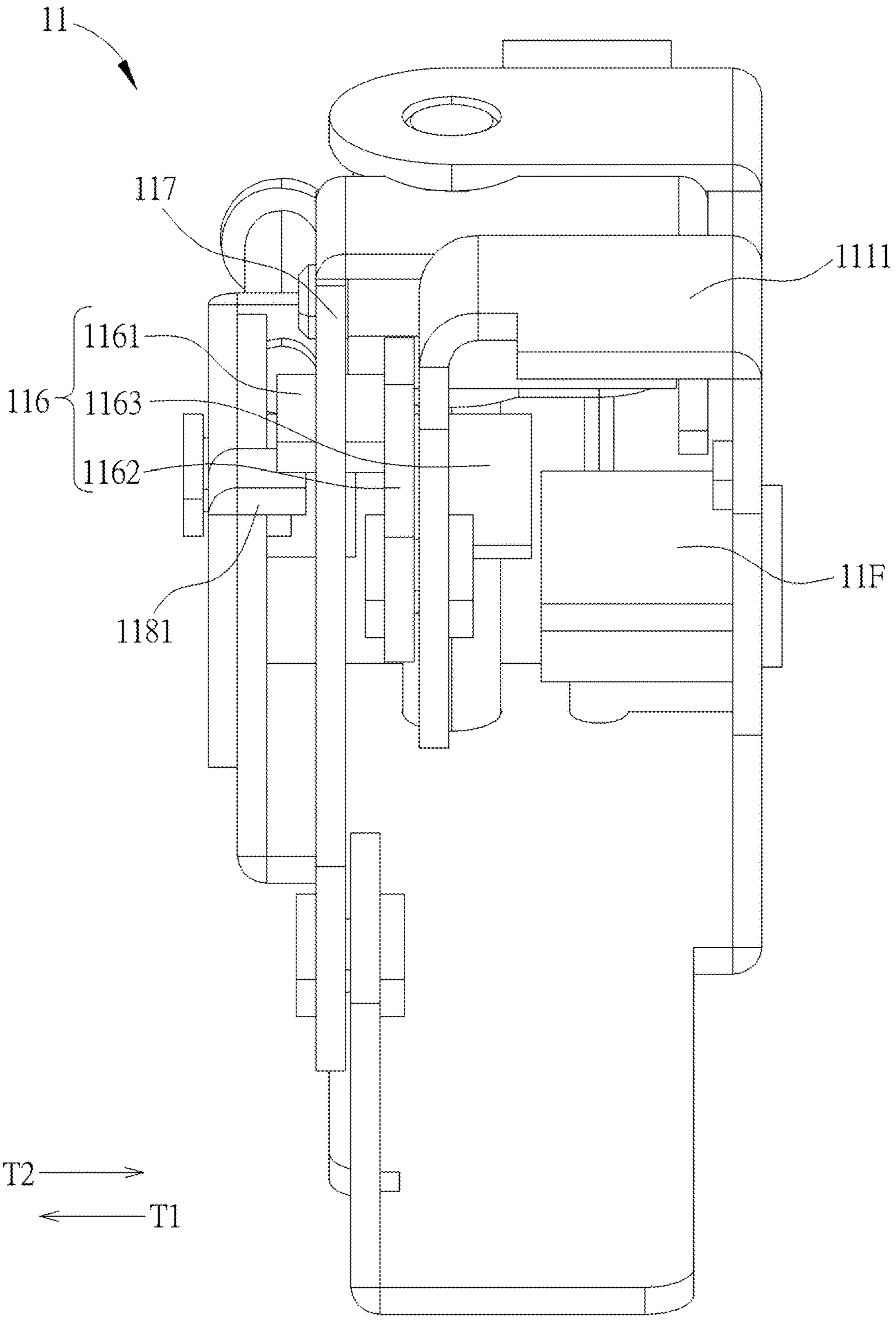
FIG. 7 is another partial diagram of the medical insertion mechanism according to the embodiment of the present invention.
Figure 8:
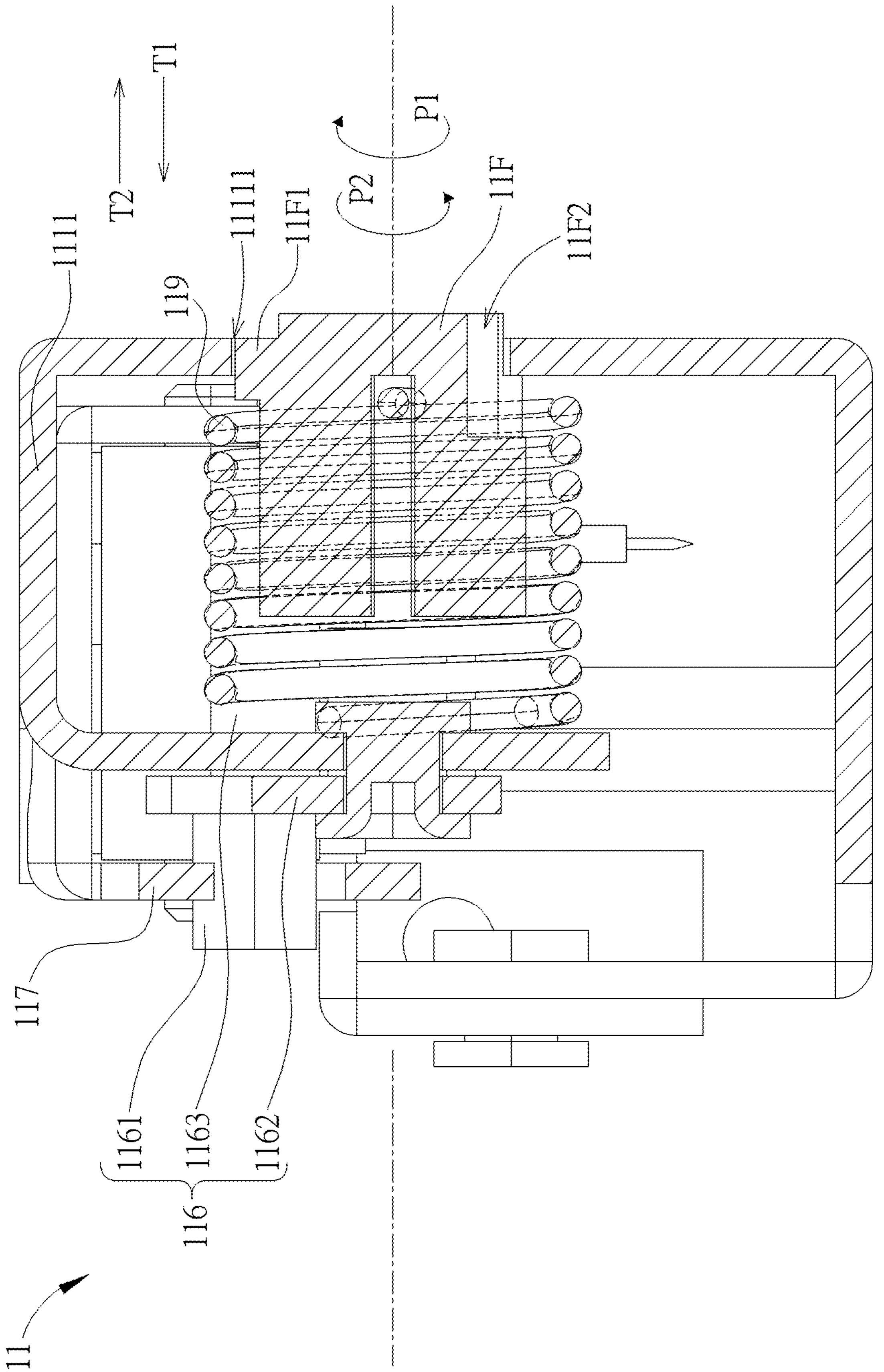
FIG. 8 is another partial sectional diagram of the medical insertion mechanism according to the embodiment of the present invention.

Please refer to FIG. 3 to FIG. 8. FIG. 7 is another partial diagram of the medical insertion mechanism 11 according to the embodiment of the present invention. FIG. 8 is another partial sectional diagram of the medical insertion mechanism 11 according to the embodiment of the present invention. As shown in FIG. 3 to FIG. 8, the medical insertion mechanism 11 further includes a column component 11F detachably installed on the base 111 and for resiliently deforming the driving component 119. In this embodiment, the driving component 119 can be a spring at least partially sleeved on the column component 11F, and two ends of the driving component 119 can respectively abut against the pivoting assembly 116 and the column component 11F (as shown FIG. 8). However, the present invention is not limited to this embodiment. For example, in another embodiment, two ends of the driving component can be respectively inserted into the column component and the pivoting body.

Specifically, please referred to FIG. 8, the column component 11F and the driving component 119 are located at the first side of the lever 117. An end of the driving component 119 is inserted into the column component 11F, and another end of the driving component 119 abuts against a surface of the stopping structure 1163 of the pivoting assembly 116. The column component 11F can be moved along a disengaging direction T1 perpendicular to the unlocking direction L1 and the insertion direction D1 for resiliently compressing the driving component 119 along the disengaging direction T1, or the column component 11F can be pivoted along a second pivoting direction P2 opposite to the first pivoting direction P1 for pivoting the pivoting assembly 116 along the second pivoting direction P2 and resiliently twisting the driving component 119. The base 111 includes an accommodating portion 1111 for at least partially receiving the column component 11F. A length of the column component 11F along a direction parallel to the disengaging direction T1 can be less than a length of the accommodating portion 1111 along the direction parallel to the disengaging direction T1, so that the column component 11F is movable relative to the accommodating portion 1111 along the disengaging direction T1. The column component 11F includes a first locking structure 11F1. The accommodating portion 1111 includes a second locking structure 11111. A pivoting movement of the column component 11F is restrained by an engagement of the first locking structure 11F1 and the second locking structure 11111, and a disengagement of the first locking structure 11F1 and the second locking structure 11111 allows the pivoting movement of the column component 11F when the column component 11F moves along the disengaging direction T1 relative to the accommodating portion 1111 to disengage the first locking structure 11F1 from the second locking structure 11111.

In this embodiment, the length of the accommodating portion 1111 along the direction parallel to the disengaging direction T1 can be less than a length of the driving component 119 along the direction parallel to the disengaging direction T1. In such a way, the driving component 119 can not only be resiliently twisted by the column component 11F to generate a first resilient force for driving the pivoting assembly 116 to pivot along the first pivoting direction P1 but also be resiliently compressed along the disengaging direction T1 to generate a second resilient force for driving the column component 11F to move along an engaging direction T2 opposite to the disengaging direction T1 relative to the accommodating portion 1111 due to the first locking structure 11F1 engaged with the second locking structure 11111.

Besides, in order for easy manual operation, an operating recess 11F2 is formed on the column component 11F for insertion of a hand tool, such as a screw driver or a hex key, to move the column component 11F along the disengaging direction T1 for disengaging the first locking structure 11F1 from the second locking structure 11111 and to pivot the column component 11F along the second pivoting direction P2 for pivoting the pivoting assembly 116 along the second pivoting direction P2 and resiliently twisting the driving component 119.

Figure 9:
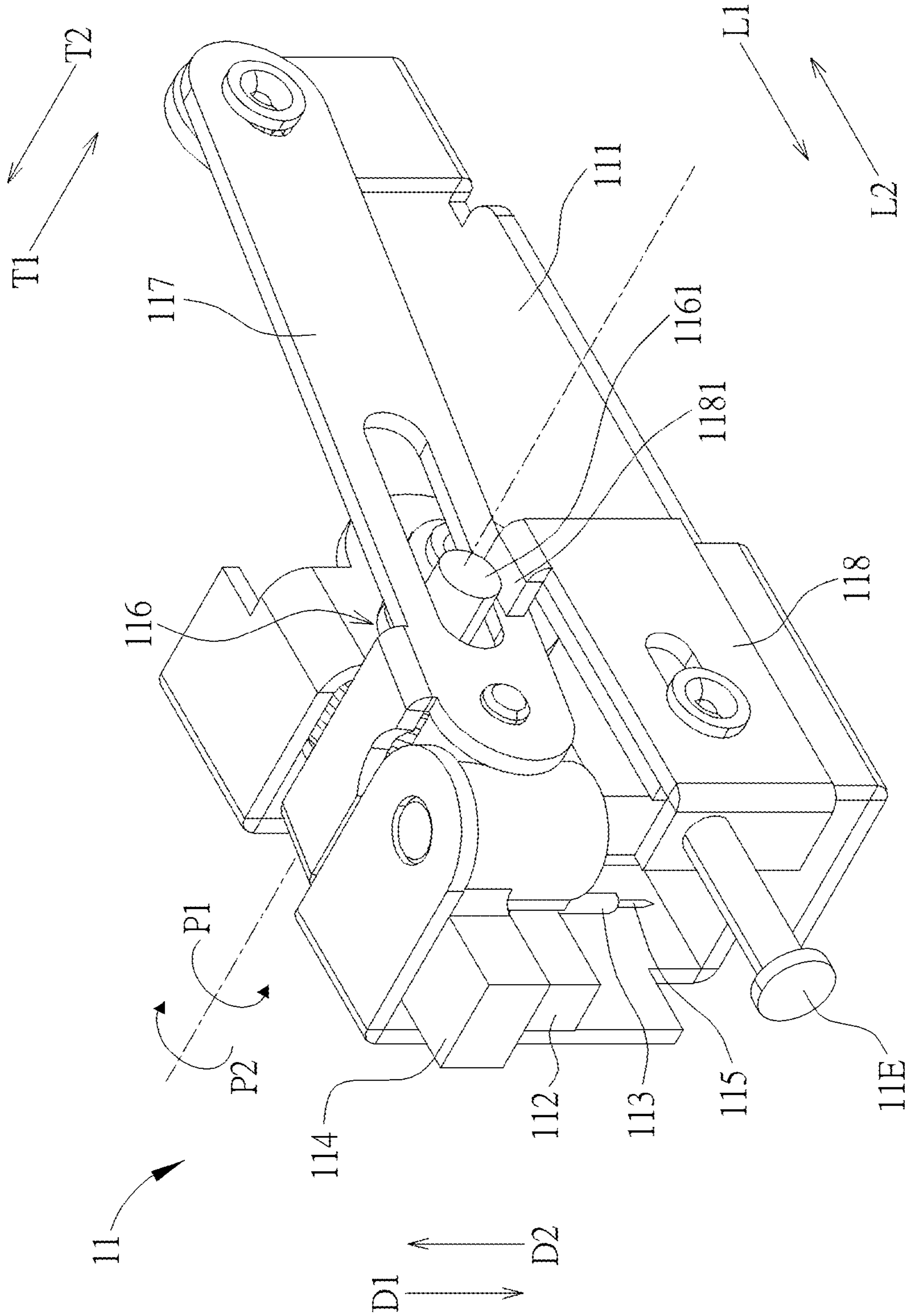
FIG. 9 is a partial diagram of the medical insertion mechanism in a first state according to the embodiment of the present invention.
Figure 11:
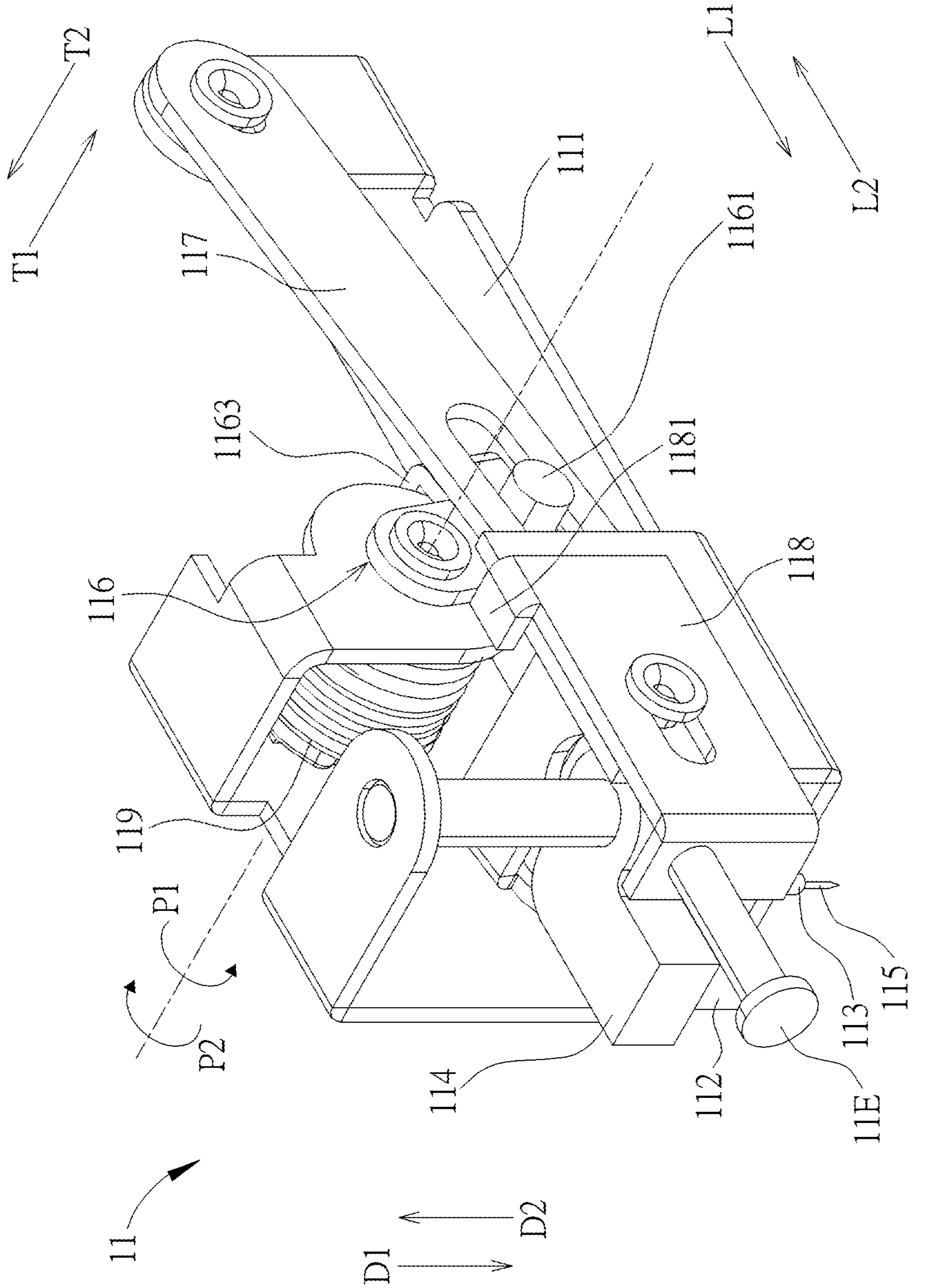
FIG. 11 is a partial diagram of the medical insertion mechanism in a third state according to the embodiment of the present invention.

Please refer to FIG. 9 to FIG. 12. FIG. 9 is a partial diagram of the medical device 1 in a first state according to the embodiment of the present invention. FIG. 10 is a partial diagram of the medical insertion mechanism 11 in a second state according to the embodiment of the present invention. FIG. 11 is a partial diagram of the medical insertion mechanism 11 in a third state according to the embodiment of the present invention. FIG. 12 is a partial diagram of the medical insertion mechanism 11 in a fourth state according to the embodiment of the present invention. As shown in FIG. 8 and FIG. 9, in order to set the medical device 1 in the first state, the column component 11F can be operated by the hand tool to move along the disengaging direction T1 for resiliently compressing the driving component 119, so as to disengage the first locking structure 11F1 from the second locking structure 11111. When the first locking structure 11F1 is disengaged from the second locking structure 11111, the column component 11F can be further operated to pivot along the second pivoting direction P2 for driving the driving component 119 to move to a first position as shown in FIG. 9 and for resiliently twisting the driving component 119. Afterwards, the column component 11F can be driven by the driving component 119 to move along the engaging direction T2, and the operating component 11E can be operated to slide the actuator 118 to a locking position as shown in FIG. 9, so that the abutting structure 1181 of the actuator 118 engages with the protruding structure 1161 of the pivoting assembly 116.

When it is desired to use the medical device 1, the operating component 11E can be operated to drive the actuator 118 to slide from the locking position as shown in FIG. 9 to an unlocking position as shown in FIG. 10 for slidably disengaging the abutting structure 1181 of the actuator 118 from the protruding structure 1161 of the pivoting assembly 116. When the abutting structure 1181 of the actuator 118 is disengaged from the protruding structure 1161 of the pivoting assembly 116, the driving component 119 can drive the pivoting assembly 116 to pivot along the first pivoting direction P1 until the stopping structure 1163 contacts with the base 111, i.e., to pivot from the first position as shown in FIG. 10 through a second position as shown in FIG. 11 to a third position as shown in FIG. 12. When the pivoting assembly 116 pivots from the first position as shown in FIG. 10 to the second position as shown in FIG. 11, the pivoting assembly 116 drives the lever 117 to drive the needle holder 114 to slide from the original position along the insertion direction D1 to push the cannula holder 112 to slide relative the base 111 together with the needle holder 114 by the pushing structure 1141, which is shown in FIG. 4, for the insertion of the needle 115 and the cannula 113 into the patient's body along the insertion direction D1. When the pivoting assembly 116 pivots from the second position as shown in FIG. 11 to the third position as shown in FIG. 12, the pivoting assembly 116 drives the lever 117 to drive the needle holder 114 to slide back to the original position along the retraction direction D2, so as to drive the needle 115 to retract relative to the cannula 113 along the retraction direction D2 for withdrawing the needle 115 from the patient's body along the retraction direction D2 and leaving the cannula 113 inserted into the patient's body.

Figure 13:
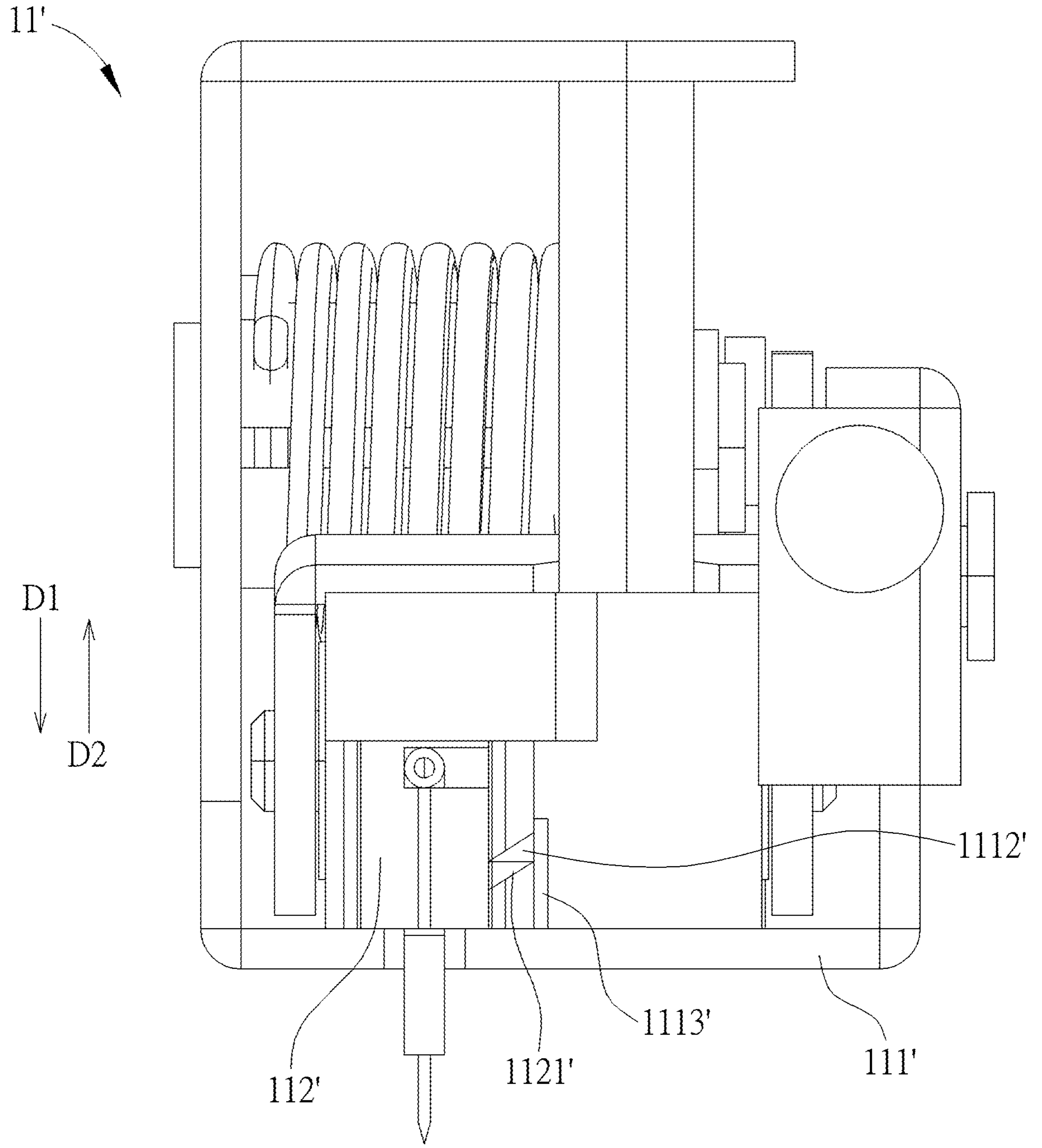
FIG. 13 and FIG. 14 are partial diagrams of a medical insertion mechanism in different states according to another embodiment of the present invention.
Figure 14:
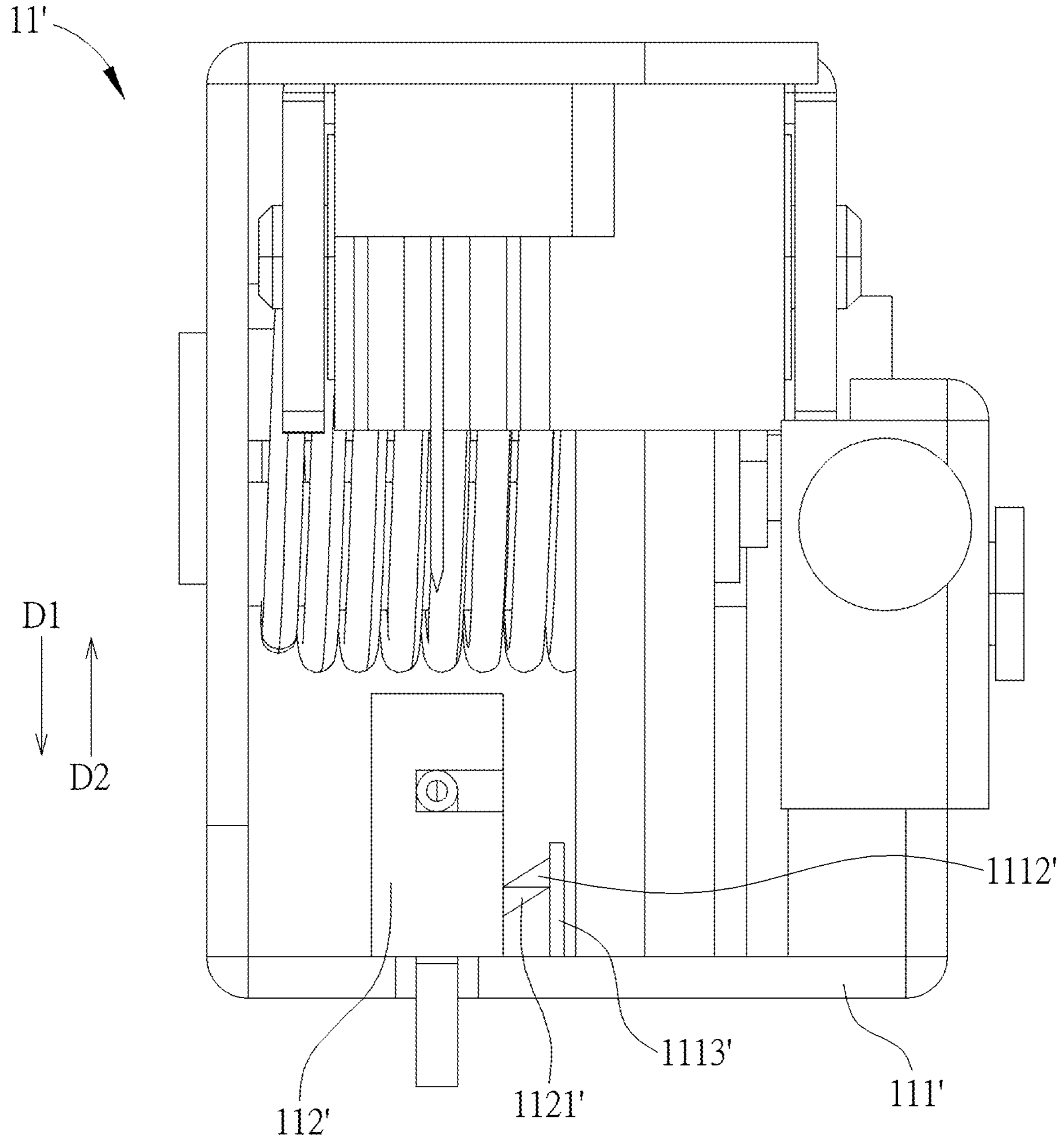

Please refer to FIG. 13 and FIG. 14. FIG. 13 and FIG. 14 are partial diagrams of a medical insertion mechanism 11' in different states according to another embodiment of the present invention. As shown in FIG. 13 and FIG. 14, different from the above-mentioned embodiment, the cannula holder 112' includes a first engaging structure 1121'. The base 111' includes an engaging hook having a second engaging structure 1112' and a resilient arm 1113'. The second engaging structure 1112' is disposed on the resilient arm 1113'. The resilient arm 1113' can be resiliently deformed by an abutment of the first engaging structure 1121' and the second engaging structure 1112' for allowing the first engaging structure 1121' to pass over the second engaging structure 1112' when the cannula holder 112' moves along the insertion direction D1, and a sliding movement of the cannula holder 112' along the retraction direction D2 is restrained by an engagement of the first engaging structure 1121' and the second engaging structure 1112'. Other details of this embodiment are similar to the ones of the above-mentioned embodiment. Detailed description is omitted herein for simplicity.

In contrast to the prior art, the present invention has less parts and compact size. Besides, in the present invention, when it is desired to use the medical device for drug injection or fluid drainage, it only has to operate the operating component to drive the actuator to slide for slidably disengaging the abutting structure of the actuator from the protruding structure of the pivoting assembly, so that the cannula can be inserted into the patient's body. Therefore, the present invention has easy operation and precise insertion and retraction function.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A medical insertion mechanism comprising:

a base;

a needle holder disposed on the base and slidable relative to the base along an insertion direction or a retraction direction opposite to the insertion direction, the needle holder comprising a pushing structure;

a needle disposed on the needle holder;

a cannula holder arranged at a position corresponding to the needle holder, the pushing structure being configured to abut against the cannula holder along the insertion direction;

a cannula disposed on the cannula holder;

a pivoting assembly disposed on the base and pivotable relative to the base from a first position through a second position to a third position;

a lever movably disposed on the base and movably engaged with the pivoting assembly and the needle holder;

an actuator disposed on the base, the actuator comprising an abutting structure configured to slidably engage with or disengage from the pivoting assembly; and a driving component configured to drive the pivoting assembly to pivot from the first position through the second position to the third position when the abutting structure slidably disengages from the pivoting assembly;

wherein when the pivoting assembly pivots from the first position to the second position, the lever drives the needle holder and the cannula holder to slide along the insertion direction, so as to drive the needle and the cannula to move along the insertion direction together;

wherein when the pivoting assembly pivots from the second position to the third position, the lever drives the needle holder to slide along the retraction direction to drive the needle to retract relative to the cannula.

2. The medical insertion mechanism of claim 1, wherein the lever is located between the pivoting assembly and the actuator.

3. The medical insertion mechanism of claim 1, wherein the pivoting assembly is engaged with a longitudinal slot formed on a middle portion of the lever between a first end and a second end of the lever.

4. The medical insertion mechanism of claim 3, wherein the longitudinal slot is adjacent to the second end of the lever and away from the first end of the lever, and the pivoting assembly comprises a protruding structure passing through the longitudinal slot and movable relative to the longitudinal slot.

5. The medical insertion mechanism of claim 1, wherein one and another one of an elongated hole and a circular hole are respectively formed on a first end and a second end of the lever, the medical insertion mechanism further comprises a connecting pin disposed on the base and a driving pin disposed on the needle holder, the connecting pin passes through the one of the elongated hole and the circular hole and is movable relative to the one of the elongated hole and the circular hole, and the driving pin passes through the another one of the elongated hole and the circular hole and is movable relative to the another one of the elongated hole and the circular hole.

6. The medical insertion mechanism of claim 1, wherein the pivoting assembly comprises a protruding structure, and the abutting structure is configured to abut against the protruding structure.

7. The medical insertion mechanism of claim 6, wherein a longitudinal slot is formed on a middle portion of the lever between a first end and a second end of the lever, the lever has a first side and a second side, the abutting structure is located at the second side of the lever, the pivoting assembly further comprises a pivoting body located at the first side of the lever, and the protruding structure protrudes from the pivoting body, passes through the longitudinal slot and is movable relative to the longitudinal slot.

8. The medical insertion mechanism of claim 1, further comprising a guiding component disposed on the base and configured to guide the needle holder and the cannula holder to slide.

9. The medical insertion mechanism of claim 8, wherein the lever is engaged with a portion of the needle holder located between the pivoting assembly and the guiding component.

10. The medical insertion mechanism of claim 1, wherein the base comprises an engaging hook configured to engage with the cannula holder for restraining a sliding movement of the cannula holder.

11. The medical insertion mechanism of claim 1, further comprising a column component detachably installed on the base and for resiliently deforming the driving component, the driving component being a spring at least partially sleeved on the column component, and two ends of the driving component respectively abut against the pivoting assembly and the column component.

12. The medical insertion mechanism of claim 11, wherein the base comprises an accommodating portion for at least partially receiving the column component, a length of the column component is less than a length of the accommodating portion, the column component comprises a first locking structure, the accommodating portion comprises a second locking structure, a pivoting movement of the column component is restrained by an engagement of the first locking structure and the second locking structure, and a disengagement of the first locking structure and the second locking structure allows the pivoting movement of the column component when the column component moves relative to the accommodating portion to disengage the first locking structure from the second locking structure.

13. The medical insertion mechanism of claim 12, wherein the length of the accommodating portion is less than a length of the driving component, and the driving component drives the column component to move relative to the accommodating portion to engage the first locking structure with the second locking structure.

14. The medical insertion mechanism of claim 11, wherein an operating recess is formed on the column component.

15. The medical insertion mechanism of claim 11, wherein the column component, the driving component, the cannula holder and the needle holder are located at a first side of the lever, and the abutting structure is located at a second side of the lever.

16. The medical insertion mechanism of claim 1, wherein the pivoting assembly comprises a stopping structure configured to contact with the base for stopping the pivoting assembly when the pivoting assembly pivots from the first position to the third position.

17. The medical insertion mechanism of claim 1, wherein the lever is driven by the pivoting assembly to drive the needle holder to slide from an original position along the insertion direction and then back to the original position along the retraction direction when the pivoting assembly pivots from the first position to the third position.

18. The medical insertion mechanism of claim 1, wherein a sliding slot is formed on the actuator, the medical insertion mechanism further comprises a sliding pin disposed on the base, and the sliding pin passes through the sliding slot and is movable relative to the sliding slot.

19. The medical insertion mechanism of claim 1, further comprising an operating component connected to the actuator.

20. A medical device comprising:

a case; and a medical insertion mechanism comprising:

- a base disposed on the case;
- a needle holder disposed on the base and slidable relative to the base along an insertion direction or a retraction direction opposite to the insertion direction, the needle holder comprising a pushing structure;
- a needle disposed on the needle holder;
- a cannula holder arranged at a position corresponding to the needle holder, the pushing structure being configured to abut against the cannula holder along the insertion direction;
- a cannula disposed on the cannula holder;
- a pivoting assembly disposed on the base and pivotable relative to the base from a first position through a second position to a third position;
- a lever movably disposed on the base and movably engaged with the pivoting assembly and the needle holder;
- an actuator disposed on the base, the actuator comprising an abutting structure configured to slidably engage with or disengage from the pivoting assembly; and
- a driving component configured to drive the pivoting assembly to pivot from the first position through the second position to the third position when the abutting structure slidably disengages from the pivoting assembly;
- wherein when the pivoting assembly pivots from the first position to the second position, the lever drives the needle holder and the cannula holder to slide along the insertion direction, so as to drive the needle and the cannula to move along the insertion direction together;
- wherein when the pivoting assembly pivots from the second position to the third position, the lever drives the needle holder to slide along the retraction direction to drive the needle to retract relative to the cannula.

* * * * *